United States Patent [19]

Sugimachi et al.

[11] Patent Number: 5,141,847
[45] Date of Patent: Aug. 25, 1992

[54] METHOD AND APPARATUS FOR PRODUCING PULSATION

[75] Inventors: Keizo Sugimachi; Kenji Takenaka; Mitsuo Shimada, all of Fukuoka; Kengo Fukuzawa, Ohita; Takashi Nishizaki; Tetsuo Ikeda, both of Fukuoka; Atsushi Yoshihara, Tokyo, all of Japan

[73] Assignee: Kureha Chemical Industry Co., Ltd., Tokyo, Japan

[21] Appl. No.: 482,231

[22] Filed: Feb. 20, 1990

[30] Foreign Application Priority Data

Aug. 18, 1989 [JP] Japan .................. 1-211237

[51] Int. Cl.$^5$ .............................................. A01N 1/02
[52] U.S. Cl. ..................................... 435/1; 435/283; 137/624.13; 137/624.15
[58] Field of Search ............... 435/283, 1; 417/295, 417/301, 309; 137/624.13, 624.15

[56] References Cited

U.S. PATENT DOCUMENTS

| 1,007,894 | 11/1911 | Scheidemann | 137/624.15 |
|---|---|---|---|
| 2,250,507 | 7/1941 | Thomas et al. | 137/624.13 |
| 2,254,833 | 9/1941 | Ashkenaz | 137/624.15 |
| 2,965,119 | 12/1960 | Hawkinson et al. | 417/309 |
| 3,156,537 | 11/1964 | McLeod | 137/624.15 |
| 3,211,179 | 10/1965 | Lilly et al. | 137/624.15 |
| 3,632,473 | 1/1972 | Belzer et al. | 435/1 |
| 3,639,084 | 2/1972 | Goldhaber | 435/283 |
| 3,738,914 | 6/1973 | Thorne et al. | 435/283 |
| 3,914,954 | 10/1975 | Doerig | 435/1 |
| 4,250,872 | 2/1981 | Tamari | 600/16 |
| 4,473,637 | 9/1984 | Guibert | 435/1 |
| 4,598,697 | 7/1986 | Numazawa et al. | 600/17 |
| 4,779,642 | 10/1988 | Wood et al. | 137/624.13 |

OTHER PUBLICATIONS

Grossi et al., Surgery (USA) 98(3), pp. 547-554, (1985) abstract.

Primary Examiner—James C. Housel
Assistant Examiner—William Chan
Attorney, Agent, or Firm—Rosen, Dainow & Jacobs

[57] ABSTRACT

In an apparatus which applies periodic pulsation to a solution flowing through a conduit while undergoing perfusion by a pump, a first valve is disposed in the conduit downstream of the pump, a bypass line is provided to the conduit downstream of the first valve, and a second valve is disposed in the bypass line for withdrawing some of a first pulsed flow formed in the conduit by opening and closing the first valve, through the bypass line as a second pulsed flow. A valve driving circuit periodically opens and closes the first valve and second valve at predetermined time schedules so that the second pulsed flow is superimposed upon the first pulsed flow to form a waveform in the conduit. Any desired pulsatile waveform can be obtained by adjusting the pulse width, the crest values, the delay time, etc., of the two pulsed flows.

22 Claims, 5 Drawing Sheets

METHOD AND APPARATUS FOR PRODUCING PULSATION

BACKGROUND OF THE INVENTION

This invention finds use in the field of medicine and relates to a method and apparatus for applying periodic pulsation to a liquid flowing through a liquid-feed conduit.

A low-temperature perfusion preservation method is known as a method of preserving a surgically removed living organ such as the liver, heart, pancreas and kidney until the organ is implanted. This is a method of prolonging the survival period of the living organ by controlling the tissue metabolism of the organ at a low temperature of 3°-10° C., perfusing an oxygenated perfusate through the artery and/or portal vein of the organ while the amount of oxygen consumed is kept low, replenishing the organ with oxygen and nutrients that are particularly required by the organ, and removing metabolic waste matter.

In this method of preserving said organ having a vascular system, perfusing the oxygenated perfusate sufficiently up to the periphery of the vascular system is particularly important in terms of maintaining the function of the organ. In order to achieve this peripheral perfusion, a pulsatile flow is more effective than a steady flow as a method of supplying the perfusate since the pulsatile flow makes it possible to obtain a high pressure sufficient for opening the capillary vessels of the organ constricted by low temperature.

Furthermore, even in cases where blood is perfused through the artery of a living body, a pulsatile flow approximating the normal blood flow waveform (the condition of the living body) is better in terms of the effects on the living body than a steady flow as a method of supplying the blood.

In order to attain these ends, a number of apparatus have been proposed in the prior art for the purpose of providing pulsation to a liquid flowing through tubing. For example, U.S. Pat. No. 4,598,697 discloses a pump apparatus for feeding blood, in which the blood is forced to pulsate by intermittently rotating rollers of a roller-type pump, by a prescribed angle, and U.S. Pat. Nos. 3,639,084 and 4,250,872 disclose an apparatus in which a pulsatile flow is produced in tubing by pressing a flexible tube, which constitutes part of a conduit, by a high-pressure fluid such as air or oxygen.

Figure 5A:
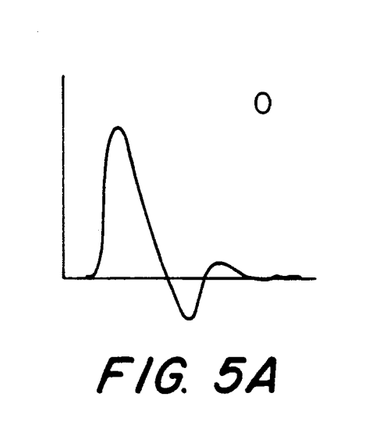
FIGS. 5(A)–(E) are diagrams respectively showing classified types of blood-flow waveforms seen at peripheral arteries such as the thigh artery with the progress of the arterial obliteration.
Figure 5B:
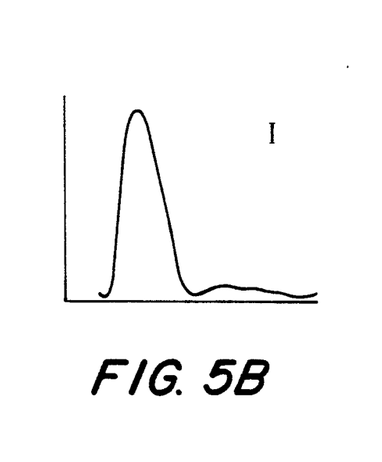
Figure 5C:
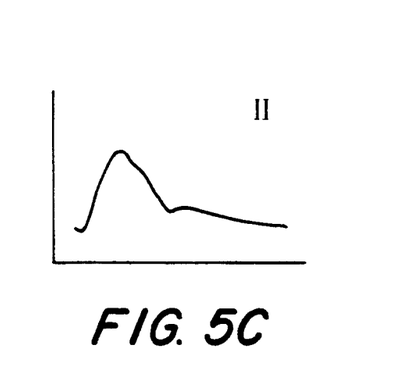
Figure 5D:
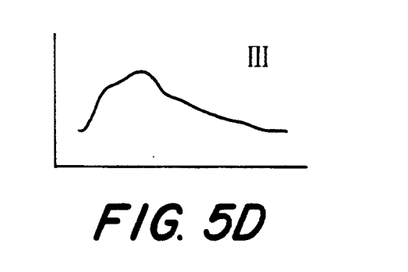
Figure 5E:
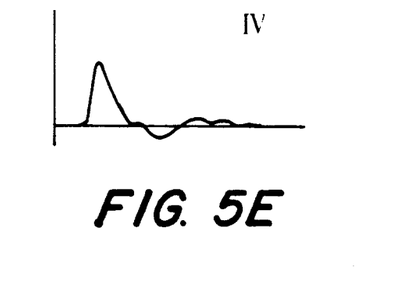

Pulsation internally of the artery of a living body can be classified into several forms depending upon the waveform of the pulsation. For example, as shown in FIG. 5 of the accompanying drawings (in each of the drawings, the abscissa corresponds to the time and the ordinate corresponds to the blood flow rate measured by utilizing the Doppler effect or an electromagnetic flow meter), blood flow waveforms of a peripheral artery affected by arterial obliteration can be classified broadly into five types. FIG. 5(A) is referred to as a 0-type waveform in which a back-flow waveform exists. This is a normal waveform in the thigh artery. With the progress of arterial obliteration, the waveform of blood flow gradually changes in the manner of FIGS. 5(B), (C), (D) and (E), where the waveforms are referred to as types I, II, III and IV, respectively. The type-I waveform is characterized in that the back-flow waveform has vanished from the normal waveform, and the waveforms from the type-II waveform onward are characterized by gradual decreasing and flattening of the wave crest and a gentler slope of the descending leg.

The present invention is based on the belief that the waveform of perfusion is related to the functional maintenance of microcirculation in the hepatic artery under low temperatures. The inventors have conducted vigorous research into the relationship between preservation of an extracted liver and the waveform of perfusion based on the classification of blood-flow waveform, shown in FIG. 5, which characterizes the arterial obliteration seen at peripheral arteries such as the thigh artery. As a result of this research, it has been found that though the normal waveform of blood supplied to the hepatic artery in a living body approximates the type-II waveform of FIG. 5, perfusion of the hepatic artery by a pulsatile waveform of types 0 through II, and preferably of types 0 and I, provides for excellent preservation effect on the liver when the low-temperature preservation of the extracted liver is employed.

In the conventional apparatus mentioned above, however, a waveform obtained thereby is not widely controllable for lack of controlling waveform distortion, described below, and it is impossible to obtain pulsation of the 0 type in such a manner that the aforementioned back-flow wave will appear.

SUMMARY OF THE INVENTION

With the foregoing in mind, it is an object of the present invention to provide a method and apparatus for producing any desired pulsatile waveform, which includes a pulsatile waveform such as of the O-type exhibiting back flow, by adjustably applying pulsation to a liquid flowing through a conduit and making it possible to readily control the waveform over a wide range in taking account of waveform distortion ascribable to the inertia of a drive unit and the elasticity of the conduit, described below.

According to the present invention, the foregoing object is attained by providing a method of producing pulsation comprising the steps of perfusing a solution through a perfusion line by pump means, forming a first pulsed flow in the perfusion line of the solution by periodically opening and closing the perfusion line at predetermined times and repetition frequency, and converting a waveform of the flow in the perfusion line into a predetermined pulsatile waveform by withdrawing some of the first pulsed flow from the perfusion line through a bypass line as a second pulsed flow by periodically opening and closing the bypass line at a predetermined time schedule.

Further, according to the invention, the foregoing object is attained by providing an apparatus which applies periodic pulsation to a solution flowing through a conduit while undergoing perfusion by pump means, comprising first valve means disposed in the conduit downstream of the pump means, a bypass line provided to the conduit downstream of the first valve means, second valve means disposed in the bypass line for withdrawing some of a first pulsed flow formed in the conduit by opening and closing the first valve means, through the bypass line as a second pulsed flow, and a valve driving circuit for controlling periodical opening and closing of the two valve means at predetermined time schedules.

In operation, the second pulsed flow, which is a back flow for the first pulsed flow, is superimposed upon the first pulsed flow, which is a forward flow. Accordingly, a pulsatile waveform having substantially any desired waveform is obtained by adjusting the pulse width, the crest values, the delay time, etc., of the two pulsed flows. It is also possible to obtain the type-0 waveform which includes the back-flow wave.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Embodiments of the present invention will now be described with reference to the accompanying drawings.

Figure 1:
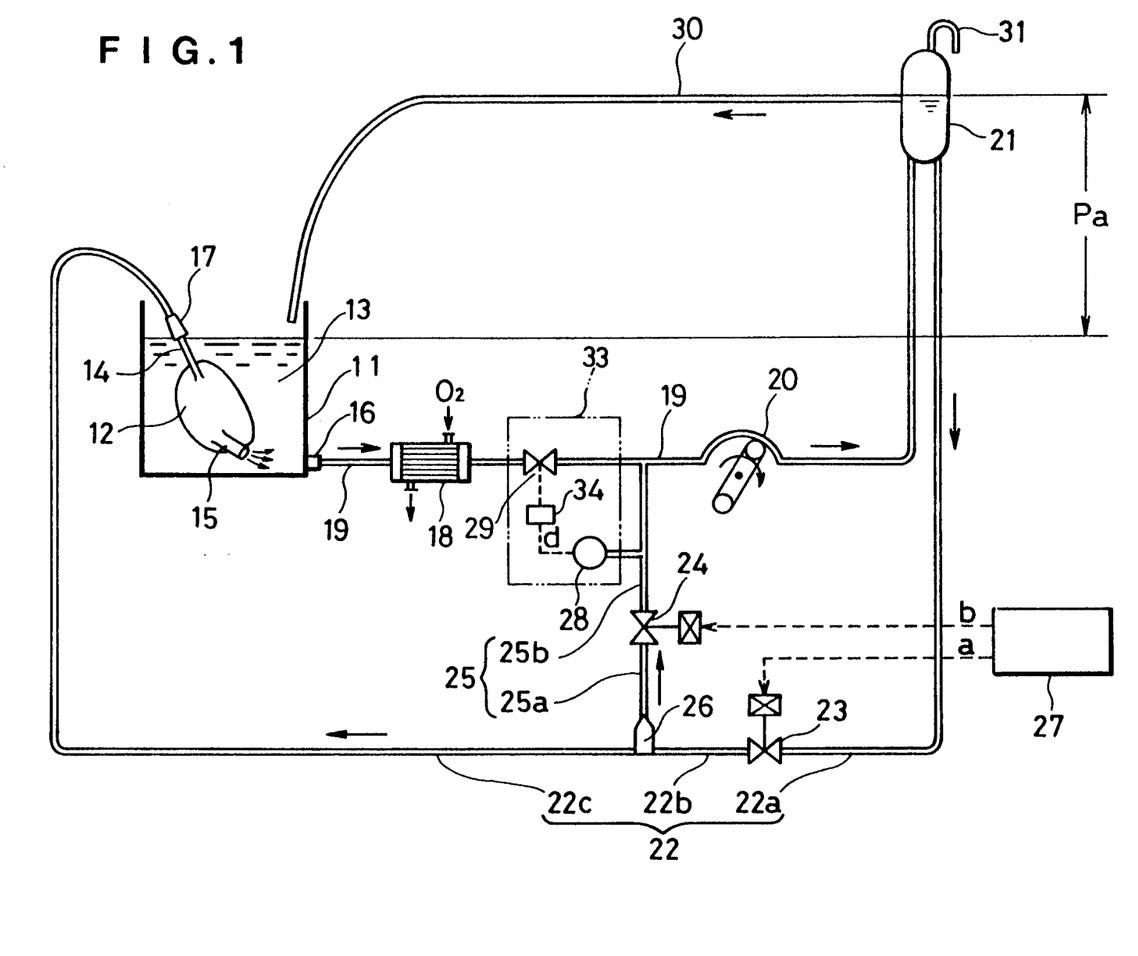
FIG. 1 is a diagram showing the arrangement of a first embodiment of an apparatus according to the present invention.

In an organ preservation system including a pulsation producing apparatus according to a first embodiment of the present invention, a chamber 11 accommodates a surgically removed organ 12 suspended in a perfusate 13. The organ 12 possesses an artery 14 and a vein 15. The lower portion of the chamber 11 is provided with an outlet port 16 for drawing the perfusate 13 out. Preferably, the chamber 11 is designed to be airtight in order to prevent the contamination of microorganisms and dust contained in the outside air.

Though the state of the organ 12 suspended in the perfusate 13 as illustrated is preferred in order to mitigate the influence of gravity upon the cells and blood vessels of the organ 12, the present invention is not limited to this arrangement. For example, a liquid reservoir (not shown) which functions to pool the perfusate 13 can be provided, making the chamber 11 empty of the perfusate 13, and the vein 15 or outlet port 16 can be connected to the liquid reservoir by tubing. Such an arrangement will make it possible to reduce the amount of perfusate 13 introduced.

The perfusate 13 should be maintained at a low temperature of 3°–10° C. in order to suppress the tissue metabolism of the organ 12 and reduce the amount of oxygen consumed. For this purpose, a system can be adopted in which a heat exchanger (not shown) is provided within the chamber 11 and a heat exchange is performed with a heat transfer medium so as to maintain the temperature of the perfusate 13 at a predetermined value. Suitable examples of the perfusate 13 are Ringer's solution, blood, blood plasma, artificial blood and Collins' solution and so on.

The perfusate 13 is pumped up from the chamber 11 to a head tank 21 by the action of pump means 20 through suction tubing 19, which is connected at one end to the outlet port 16 of the chamber 11, while the concentration of oxygen dissolved in the perfusate 13 is adjusted by a membrane-type oxygenator 18. The perfusate 13 in the head tank 21 is supplied to the artery 14 of the organ 12 via liquid-feed tubing 22 and a connection adapter 17. Overflow from the head tank 21 is returned to the chamber 11 through overflow tubing 30. The head tank 21 is vented to the atmosphere by a vent 31. Pressure Pa at which the perfusate 13 is supplied to a valve 23, described below, is regulated to a prescribed value by an elevating device (not shown) that is capable of varying the height of the head tank 21. Suitable examples of the pump means 20 are a roller-type pump, a centrifugal pump and a diaphragm pump.

The valve 23, which is a first valve means constituting a feature of the present invention, is disposed in the liquid-feed tubing 22. The valve 23 is opened and closed at predetermined times and repetition frequency by a control output "a" outputted from a valve driving circuit 27. As a result, a first pulsed flow is formed in a liquid-feed tubing member 22b on the downstream side of the valve 23.

Bypass tubing 25 is connected to the liquid-feed tubing 22 at a position downstream of the valve 23. In cooperation with a valve 24, described below, the bypass tubing 25 causes some of the first pulsed flow provided by the operation of the valve 23 to branch off so as to form a second pulsed flow in the bypass tubing 25, and, as a result, superimposes these first and second pulsed flows to form a desired pulsatile waveform inside a liquid-feed tubing member 22c. One end of the bypass tubing 25 in FIG. 1 is coupled to the suction tubing 19 so that the second pulsed flow withdrawn as described above is recycled.

The valve 24, which is a second valve means constituting a feature of the present invention, is disposed in the bypass tubing 25 and serves as means for controlling the second pulsed flow. Opening and closing of the valve 24 is controlled by a control output "b" outputted from the valve driving circuit 27. It is allowable to adopt an arrangement in which the valves 23, 24 are general in opening (closing) manner or in which these valves operate continuously or in step-wise fashion. Examples of the valves 23, 24 are solenoid pinch valves, electromagnetic valves or valves driven by pneumatic or hydraulic pressure. Solenoid pinch valves and electromagnetic valves include those of the NO type, which are open when in the deenergized state, and the NC type, which are closed when in the deenergized state. However, if the NO type is used as the valve 23 and the NC type is used as the valve 24, perfusion of the solution can be permissibly carried out even if the valve driving circuit 27 is rendered inoperative. Furthermore, as will be described later, the valve driving circuit 27 can control the parameters which make it possible to vary the pulsatile waveform by outputting the control outputs "a" and "b". These parameters are the repetition frequency N of the waveform, the open time $t_1$ of the valve 23, the open time $t_2$ of the valve 24 and the delay time $t_d$ as the time difference between the opening operations of the two valves 23, 24. Generally, the frequencies of the control outputs "a" and "b" are identical. However, if one is made harmonic with the other, then the resultant waveform obtained by superimposing the two pulsed flows can be made to take on a variety of forms.

As shown in FIG. 1, a pressure control unit 33 for controlling the pressure within bypass tubing member 25b comprises a valve 29 capable of controlling the flow rate, for example, a servomotor-driven needle valve, disposed in the suction tubing 19, a negative-pressure gauge (equipped with a pressure setting device) 28 for outputting a difference "d" between a pressure signal detected by the pressure gauge 28 and the voltage of the setting device, and an amplifier 34 for controlling, for example, the rotation of the servomotor by an amplified difference "d". For example, on the basis of the difference "d", the amplifier 34 drives the servomotor in a direction which closes the needle valve when the pressure detected by the pressure gauge 28 is higher than the pressure set by the setting device, and in a direction which opens the needle valve when the detected pressure is lower than the set pressure. As a result, the pressure within the bypass tubing member 25b is controlled. The pressure control unit 33 provides negative pressure within the bypass tubing member 25b, namely sucking pressure by which the second pulsed flow is forced to be withdrawn from the first pulsed flow through the bypass tubing 25. Accordingly, if the setting device of the pressure gauge 28 is varied and set, the amount of the withdrawn flow can be changed.

In a case where another valve is disposed in series with the valve 29 so as to make it possible to manually regulate the abovementioned suction pressure by adjusting the other valve while observing the pressure gauge 28, an arrangement can be adopted in which a minimum flow path will exist even if this other valve is in a completely closed state. If such an arrangement is adopted, the minimum flow rate of the solution can be assured even if this other valve should be closed mistakenly. Such an arrangement assures safety. Also, such a consideration should be taken for the valve 29.

A bubble trap 26 is adapted to remove air bubbles, which may be generated in the liquid-feed tubing 22b, rapidly through the bypass tubing 25 so that these air bubbles will not be conveyed to the organ 12 while being accompanied by the perfusate 13. The bubble trap 26 is useful because if the concentration of oxygen dissolved in the perfusate 13 is high, some of the dissolved oxygen bubbles out owing to a sudden drop in pressure which develops when the solution passes through the valve 23, and these bubbles stay and accumulate in the liquid-feed tubing 22b. If there is a considerable increase in the amount of air bubbles accumulating in the liquid-feed tubing 22b, this can cause a distortion in the pulsatile waveform because of compressibility of the bubbles, which makes the waveform broaden in the direction of the time axis. It is not necessary to use the bubble trap 26 if the junction of the tubings 22 and 25 is made an inverted-Y junction or if the inner diameter of the bypass tubing 25 is enlarged at the junction.

The valve driving circuit 27 according to this embodiment will now be described with reference to FIG. 2.

Figure 2:
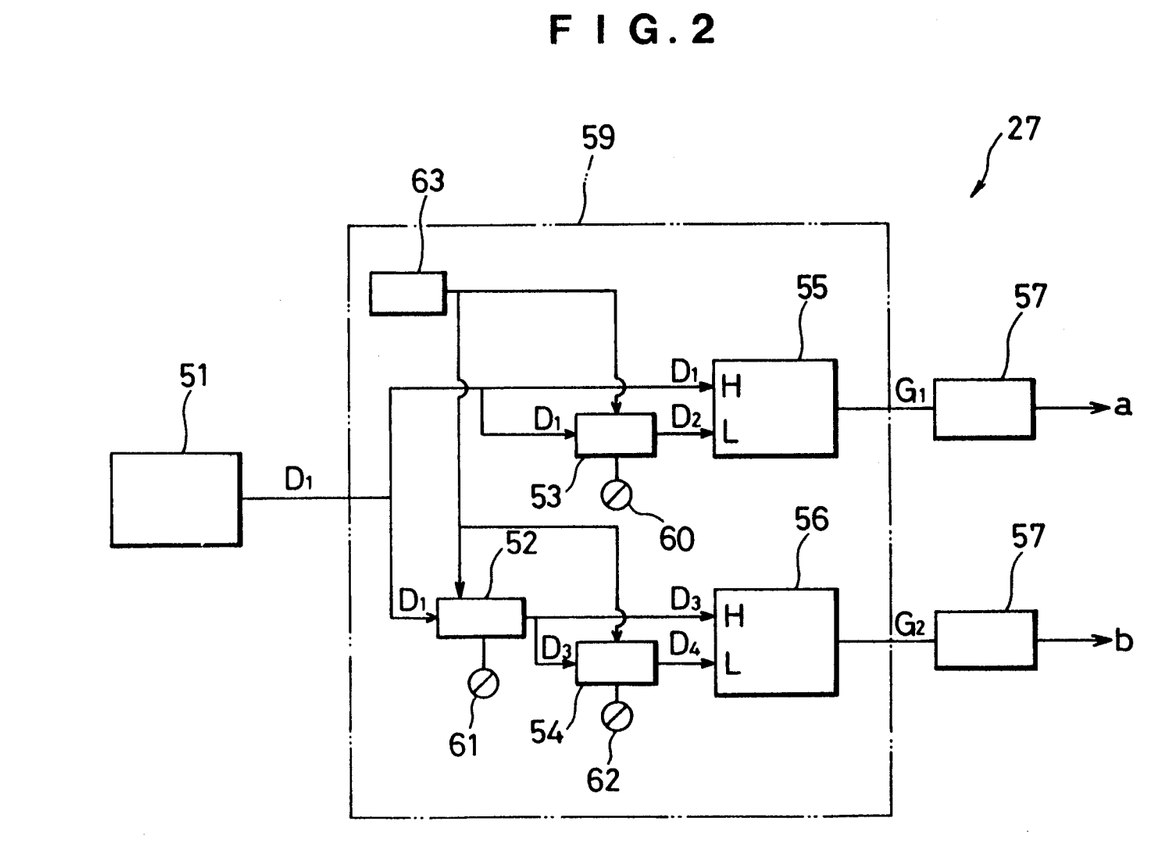
FIG. 2 is a diagram showing the construction of a valve driving circuit in the apparatus of FIG. 1.

With reference to FIG. 2, numeral 51 denotes a pulse generator for generating a trigger pulse signal $D_1$ having a predetermined pulse interval $\tau$ capable of being adjusted. The pulse interval $\tau$ provides the repetition frequency $N (=1/\tau)$, which is one of the abovementioned parameters.

As shown in FIG. 2, the trigger signal $D_1$ from the pulse generator 51 is received by a timing gate circuit 59 which comprises a standard clock 63 for generating rectangular pulses having a frequency of, e.g., 1 KHz, counters 53, 52 which start counting the rectangular pulses received thereby from the moment the trigger signal $D_1$ is inputted thereto, and which respectively generate trigger signals $D_2$, $D_3$ when the count becomes equal to pulse numbers set by adjusting devices 60, 61, respectively, a counter 54 which starts counting the rectangular pulses received thereby from the moment the signal $D_3$ outputted from counter 52 is inputted thereto, and which generates a trigger signal $D_4$ when the count becomes equal to the pulse number set by an adjusting device 62, and gate circuits 55, 56 which generate respective gate pulse signals G1, G2 whose TLL level is "1" (high) from the moment an ON trigger enters the respective H terminal until the moment an OFF trigger enters the respective L terminal. The counters 52-54 in the timing gate circuit 59 function as delay circuits which delay the input signal, and the delay times of these counters are adjusted by the respective adjusting devices 60-62.

Relay switching circuits 57 and 58 open and close, e.g., TTL-driven solid-state relays (SSRs) upon receiving the TTL gate signals $G_1$ and $G_2$, thereby producing the control outputs "a", "b" which control the valves 23 and 24, respectively, Accordingly, the aforementioned parameters $t_1$, $t_2$ and $t_d$ can be adjusted by the adjusting devices 60, 62 and 61, respectively.

An organ preservation apparatus according to a second embodiment of the present invention will now be described with reference to FIG. 3. The essential difference between the apparatus of this embodiment and that shown in FIG. 1 is the method of controlling the perfusing pressure at which the perfusate 13 is supplied to the valve 23 and the suction pressure in the bypass tubing member 25b.

Figure 3:
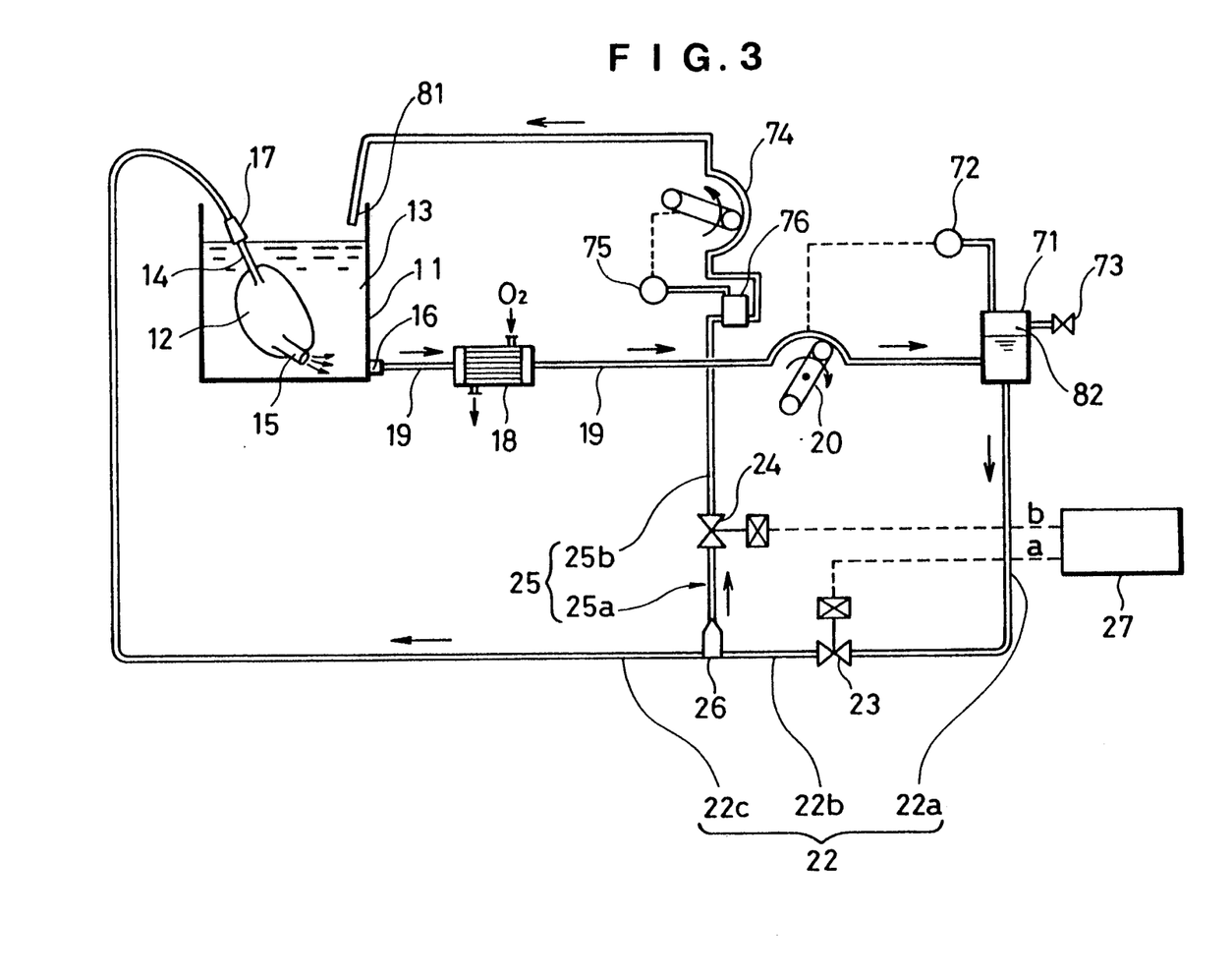
FIG. 3 is a diagram showing the arrangement of a second embodiment of an apparatus according to the present invention.

As shown in FIG. 3, a pressure buffer 71 is provided as means which utilizes the compressibility of air to buffer a fluctuation of delivery pressure caused by pulse-like pumping of the pump means 20 such as a roller-type pump. The amount of air 82 sealed in the pressure buffer 71 is regulated by a cock 73. A pressure gauge (equipped with a pressure setting device) 72 is connected to the pressure buffer 71. The operation of the pump means 20 is controlled by a relay circuit incorporated in the pressure gauge 72 and responsive to a pressure difference between the pressure detected by the pressure gauge 72 and the set pressure, so that the difference becomes zero.

A vacuum pot 76 is disposed in the bypass tubing member 25b, a roller pump 74 pumps solution out of the vacuum pot 76 and returns it to the chamber 11, and a negative-pressure gauge (equipped with a pressure setting device and a relay circuit) 75 is connected to the vacuum pot 76. The roller pump 74, negative-pressure gauge 75 and vacuum pot 76 are elements which function in a similar manner to the pressure control unit 33 of the first embodiment and control the aforementioned suction pressure. A relay circuit responsive to the difference between the pressure detected by the pressure gauge 75 and the set pressure is incorporated in the pressure gauge 75. A power circuit of the roller pump 74 is controlled by this relay circuit.

Pressure control will now be described in further detail. When the second pulsed flow flows into the vacuum pot 76 and causes the pressure in the vacuum pot 76 to rise above the set pressure value, the pressure gauge 75 produces relay-contact output which drives the roller pump 74. When the pressure in the vacuum pot 76 falls below the set pressure owing to the driving action of the pump 74, the pressure gauge 75 produces a relay-contact output which stops the roller pump 74. Accordingly, by manipulating the setting device incorporated in the pressure gauge 75, the pressure in the bypass tubing member 25b can be changed and set.

Pulsatile waveforms A and B obtained with the apparatus of the first and second embodiments described above are illustrated in FIG. 4. These waveforms were obtained by installing an electromagnetic flow meter in the liquid-feed tubing member 22c and recording the waveform output using a digitizing oscilloscope. Flow rate (ml/min) is plotted along the ordinate, and time (msec) is plotted along the abscissa.

Figure 4A:
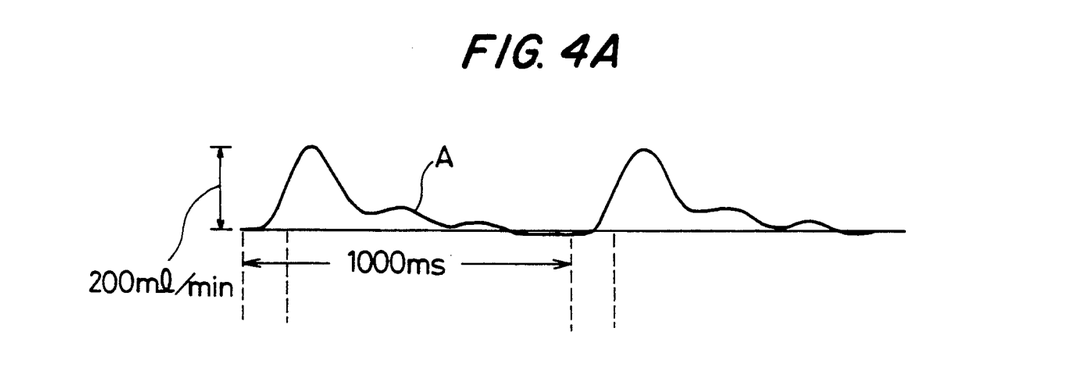
FIGS. 4a and 4B are diagrams, respectively showing the waveform of a first pulsed flow obtained with the apparatus of FIGS. 1 and 3, and a pulsatile waveform obtained with the apparatus of FIGS. 1 and 3, and also showing the open time ($t_1$) of a first valve means, a delay time ($t_d$) from the opening operating time of the valve of the first valve means to the opening operating time of a second valve means, and the open time ($t_2$) of the second valve means.
Figure 4B:
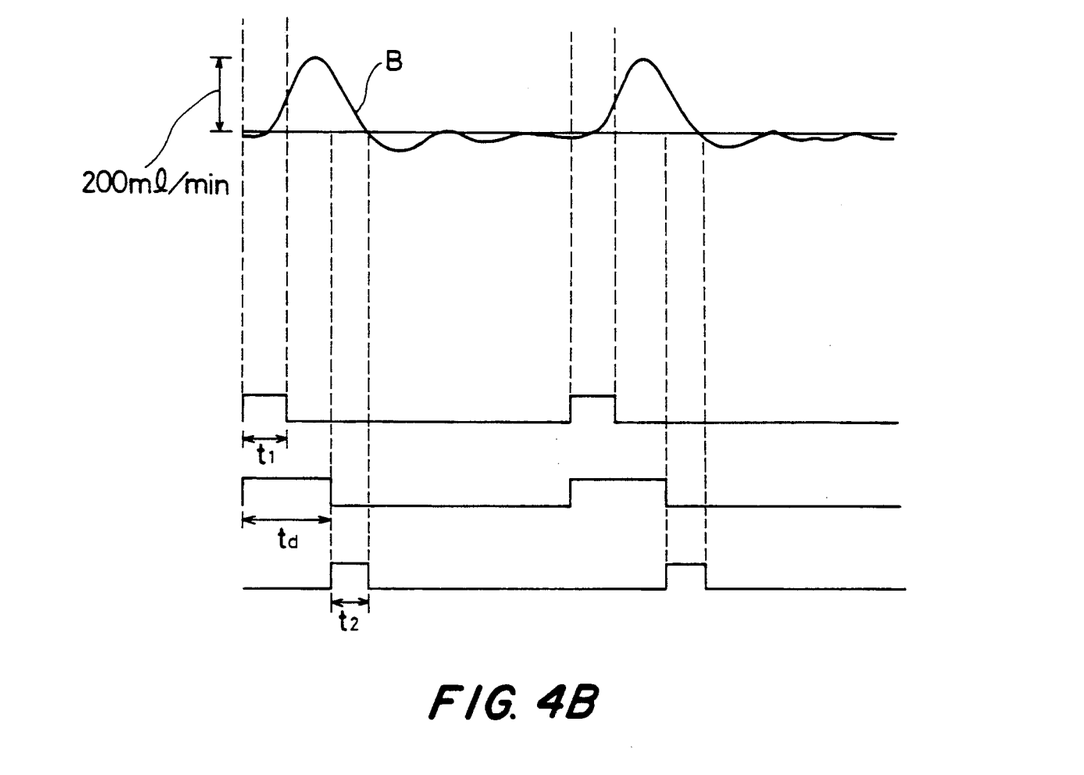

The waveform A in FIG. 4 is obtained when the valve 24 is closed and only the valve 23 is opened for the time $t_1$ by the control output "a" outputted from the valve driving circuit 27. In other words, this is the waveform of the first pulsed flow mentioned above. If the duration (about 150 msec) of the output "a" which controls the valve 23 is compared with the duration (about 700 msec) of the waveform of the flow actually formed by driving the valve 23, an enlargement in duration due to waveform distortion will be observed.

As set forth earlier, this waveform distortion is mainly ascribable to a delayed response due to the inertia of the driving parts of valve 23 and the elasticity of the flexible tubing constituting the tubing members 22b and 22c. In particular, since there is a sharp increase in pressure caused by inflow of the solution, downstream of the valve 23 at the instant this valve is opened, the flexible tubing temporarily expands and the flow does not stop completely until the expanded tubing is gradually restored to its normal state. The latter half of the waveform A exhibits distortion, namely broadening, of the waveform due to the elasticity of the tubing.

The waveform B in FIG. 4 is obtained when, in addition to the valve 23, the valve 24 is driven for the time $t_2$ by the control output "b" delayed by the time $t_d$. This waveform is the pulsatile waveform similar to the O-type shown in FIG. 5 having the back-flow waveform which is a characterizing feature of the present invention. More specifically, the difference between the waveforms A and B is the waveform of the second pulsed flow sucked through the bypass tubing 25 and controlled by the valve 24.

Thus, in accordance with the present invention, the artery of an organ can be supplied with a short-duration pulsatile flow which includes a pulsatile flow having a back-flow wave similar to that of the 0-type waveform described earlier. Accordingly, an instantaneous pressure high enough to open the capillary vessels of the organ can be produced, and the average pressure in the blood vessels can be kept low. This makes it possible to limit damage of the vascular system of the organ. As a result, it is possible to prevent edema, which is a cause of tissue damage, and the organ can be preserved for a longer period of time.

As many apparently widely different embodiments of the present invention can be made without departing from the spirit and scope thereof, it is to be understood that the invention is not limited to the specific embodiments thereof except as defined in the appended claims.

What is claimed is:

1. A method of providing a predetermined pulsed flow of a solution to an organ, comprising the steps of:
    pumping the solution through a perfusion line connected to the organ;
    periodically restricting the flow of the solution in the perfusion line to provide a first pulsed flow of the solution in the perfusion line; and
    withdrawing some of the solution in the first pulsed flow thereof from the perfusion line through a bypass line and periodically restricting the flow of the solution in the bypass line in synchronism with the changing of the flow in the perfusion line to provide the predetermined pulsed flow to the organ.

2. The method of claim 1 wherein the perfusion line and the bypass line are opened and closed to periodically restrict the flow of the solution in the respective lines.

3. The method of claim 2 wherein the bypass line is opened and closed at different times than the opening and closing of the perfusion line and in synchronism therewith.

4. The method of claim 1, further comprising the step of oxygenating the solution upstream of the pump means.

5. The method of claim 4, further comprising the step of applying suction of a prescribed pressure to the solution withdrawn through the bypass line.

6. The method of claim 4, wherein the solution is maintained at a temperature between 3° C. and 10° C.

7. The method of claim 1, further comprising the step of maintaining the solution at a temperature between 3° C. and 10° C.

8. The method of claim 1, further comprising the step of applying suction of a prescribed pressure to the solution withdrawn through the bypass line.

9. An apparatus which provides a predetermined pulsed flow of a solution to an organ, comprising:
    a conduit arrangement having an inlet and an outlet adapted to be connected to said organ to thereby enable said solution to be pumped to said organ;
    pump means connected to direct said solution from said inlet to said outlet through said conduit arrangement;
    first valve means disposed in said conduit arrangement downstream of said pump means;
    a bypass line connected between a first portion of said conduit arrangement downstream of said first valve means and a second portion of said conduit arrangement upstream of said pump means;
    second valve means disposed in said bypass line;
    valve controlling means for periodically operating said first valve means sand said second valve means in synchronism to provide a first pulsed flow of said solution in said first portion of said conduit arrangement upstream of said bypass line and said predetermined pulsed flow in said first portion of said conduit arrangement downstream of said connection of said first portion of said conduit arrangement to said bypass line,
    said apparatus further comprising an oxygenator disposed in said conduit arrangement upstream of said pump means and first valve means.

10. The apparatus of claim 9, further comprising pressure control means for controlling pressure of said solution upstream of said first valve means and pressure of said solution downstream of said second valve means within respective prescribed limits.

11. The apparatus of claim 10 wherein said pressure control means comprises means for applying suction to said solution downstream of said second valve means.

12. The apparatus of claim 9 wherein said valve controlling means comprises means for opening and closing said first and second valve means to thereby open and close said conduit arrangement and said bypass line, respectively.

13. The apparatus of claim 12 wherein said valve controlling means comprises means for opening and closing said second valve means at different times than said valve controlling means opens and closes said first valve means but in synchronism with the opening and closing of said first valve means.

14. The apparatus of claim 9 wherein said oxygenator is a membrane-type oxygenator.

15. The apparatus of claim 9 wherein said pump means comprises a roller-type pump.

16. The apparatus of claim 9 wherein said first valve means and said second valve means each comprises a solenoid pinch valve.

17. The apparatus of claim 9, further comprising an air-tight chamber for containing said organ, said chamber being connected to said inlet and said outlet of said conduit arrangement, whereby an artery side of said organ may be connected to said conduit arrangement and a vein side of said organ may communicate with the interior of said chamber.

18. The apparatus of claim 9 wherein said pump means comprises a centrifugal pump.

19. The apparatus of claim 9 wherein said pump means comprises a diaphragm pump.

20. The apparatus of claim 9 wherein said first valve means and said second valve means each comprises an electromagnetic valve.

21. The apparatus of claim 9 wherein said first valve means and said second valve means each comprises a valve driven by pneumatic pressure.

22. The apparatus of claim 9 wherein said first valve means and said second valve means each comprises a valve driven by hydraulic pressure.

* * * * *